(12) United States Patent
Brown et al.

(10) Patent No.: US 6,352,547 B1
(45) Date of Patent: Mar. 5, 2002

(54) STENT CRIMPING SYSTEM

(75) Inventors: Terry V. Brown, Fridley; Leo M. Klisch, Maple Grove, both of MN (US); Victor G. Shukhat, Canton, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/401,467

(22) Filed: Sep. 22, 1999

(51) Int. Cl.[7] .............................................. A61M 29/00
(52) U.S. Cl. ........................................... 606/198; 606/1
(58) Field of Search ................................ 623/901, 1.18, 623/1.2, 1.22, 1.23, 1.11; 606/108, 190, 194, 200, 198, 1

(56) References Cited

U.S. PATENT DOCUMENTS

| 5,026,377 A | | 6/1991 | Burton et al. ................ 606/108 |
| 5,183,085 A | | 2/1993 | Timmermans ................ 140/89 |
| 5,290,305 A | | 3/1994 | Inoue ........................ 606/191 |
| 5,306,294 A | * | 4/1994 | Winston et al. ................ 623/1 |
| 5,381,686 A | | 1/1995 | Thorup .................... 72/453.06 |
| 5,405,379 A | * | 4/1995 | Lane ............................ 623/1 |
| 5,411,521 A | | 5/1995 | Putnam et al. ............... 606/225 |
| 5,437,083 A | | 8/1995 | Williams et al. ............... 29/253 |
| 5,441,515 A | * | 8/1995 | Khosravi et al. ............... 623/1 |
| 5,509,184 A | | 4/1996 | Herrero ....................... 29/252 |
| 5,546,646 A | | 8/1996 | Williams et al. .......... 29/407.08 |
| 5,591,222 A | | 1/1997 | Susawa et al. ................. 623/1 |
| 5,626,604 A | | 5/1997 | Cottone, Jr. ................. 606/198 |
| 5,628,754 A | | 5/1997 | Shevlin et al. ............... 606/108 |
| 5,630,830 A | | 5/1997 | Verbeek ...................... 606/198 |
| 5,672,169 A | | 9/1997 | Verbeek ........................ 606/1 |
| 5,700,285 A | | 12/1997 | Myers et al. .................. 623/1 |
| 5,725,519 A | | 3/1998 | Penner et al. .................. 606/1 |
| 5,738,674 A | | 4/1998 | Williams et al. ................ 606/1 |
| 5,746,764 A | | 5/1998 | Green et al. ................. 606/194 |
| 5,749,921 A | | 5/1998 | Lenker et al. .................. 623/1 |
| 5,766,203 A | | 6/1998 | Imran et al. ................. 606/198 |
| 5,810,871 A | | 9/1998 | Tuckey et al. ............... 606/198 |
| 5,810,873 A | | 9/1998 | Morales ...................... 606/198 |
| 5,836,952 A | | 11/1998 | Davis et al. ................. 606/108 |
| 5,836,965 A | | 11/1998 | Jendersee et al. ........... 606/198 |
| 5,860,966 A | | 1/1999 | Tower ........................... 606/1 |
| 5,893,852 A | | 4/1999 | Morales ...................... 606/108 |
| 5,893,867 A | | 4/1999 | Bagaoisan et al. .......... 606/198 |
| 5,911,752 A | | 6/1999 | Dustrude et al. ............... 623/1 |
| 5,920,975 A | * | 7/1999 | Morales ........................ 29/282 |
| 5,957,929 A | * | 9/1999 | Brenneman ................. 606/108 |
| 5,972,016 A | * | 10/1999 | Morales ...................... 606/198 |
| 5,992,000 A | | 11/1999 | Humphrey et al. ........... 29/516 |
| 6,024,737 A | * | 2/2000 | Morales ......................... 606/1 |

FOREIGN PATENT DOCUMENTS

| DE | 295 06 654.7 | | 7/1995 | |
| DE | 195 32 288 A1 | | 3/1997 | |
| EP | 0 630 623 A2 | | 12/1994 | |
| EP | 0 701 800 A1 | | 3/1996 | |
| WO | 96/03092 A1 | | 2/1996 | |
| WO | 97/20593 | | 6/1997 | |
| WO | 98/19633 | | 5/1998 | |
| WO | 99/55255 | * | 11/1999 | ............. A61F/2/06 |

* cited by examiner

Primary Examiner—Cary E. O'Connor
(74) Attorney, Agent, or Firm—Vidas, Arrett & Steinkraus, P.A.

(57) ABSTRACT

A stent crimper is formed of at least one crimping member disposed in a reducible diameter loop. The crimping member includes at least one pulling member extending from the loop. The diameter of the loop is reduced by pulling on the pulling member. A stent placed in the loop may be crimped by reducing the diameter of the loop.

5 Claims, 6 Drawing Sheets

STENT CRIMPING SYSTEM

BACKGROUND OF THE INVENTION

This invention relates to an assembly and a method for fastening a stent onto a catheter. This kind of device finds routine use in the area of percutaneous transluminal coronary angioplasty (PTCA) procedures, although it may be used in other types of procedures, as well.

Stents and stent delivery assemblies are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Inflation expandable stents are well known and widely available in a variety of designs and configurations. Inflation expandable stents are crimped to their reduced diameter about the delivery catheter, then maneuvered to the deployment site and expanded to the vessel diameter by fluid inflation of a balloon positioned between the stent and the delivery catheter. The present invention is particularly concerned with the crimping of inflation expandable stents although self-expanding stent may be crimped as well.

An example of a stent is described in PCT Application NO. 960 3092 A1, published Feb. 8, 1996, the content of which is incorporated herein by reference.

In advancing a stent through a body vessel to a deployment site, the stent must be able to securely maintain its axial position on the delivery catheter, without translocating proximally or distally, and especially without becoming separated from the catheter. Stents that are not properly secured or retained to the catheter may slip and either be lost or be deployed in the wrong location or partially deployed. In securing a stent to a catheter, however, the stent must be crimped in such a way as to minimize or prevent altogether distortion of the stent and to thereby prevent abrasion and/or reduce trauma of the vessel walls.

In the past, crimping has been done by hand often resulting in the application of undesired uneven forces to the stent. Such a stent must either be discarded or re-crimped. Stents which have been crimped multiple times can suffer from fatigue and may be scored or otherwise marked which can cause thrombosis. A poorly crimped stent can also damage the underlying balloon.

Recently, stent crimping devices have been disclosed in U.S. Pat. No. 5,546,646 to Williams et al, U.S. Pat. No. 5,183,085 to Timmermans et al., U.S. Pat. No. 5,626,604 to Cottone, Jr., U.S. Pat. No. 5,725,519, to Penner et al., U.S. Pat. No. 5,810,873 to Morales, WO 97/20593 and WO 98/19633.

All U.S. patents and applications and all other published documents mentioned anywhere in this application are incorporated herein by reference in their entirety.

BRIEF SUMMARY OF THE INVENTION

In order to properly crimp a stent in accordance with the present invention it would be desirable to produce a device, optionally portable, to crimp a stent onto a catheter uniformly while minimizing the distortion of and scoring and marking of the stent and due to the crimping. This may be accomplished in the present invention, in its many embodiments, by applying an inward force to a stent mounted upon a catheter using a loop of reducible diameter.

The present invention is therefore directed to a stent crimper comprising a crimping member disposed in a reducible diameter loop with at least one pulling member extending from the loop. A stent and optionally catheter are placed in the loop and the diameter of the loop reduced by pulling on the pulling member thereby crimping the stent, optionally to the catheter.

Stent crimpers based on the loop construction may comprise a plurality of such crimping members. Desirably, a sleeve will be present between the crimping member and the stent to protect the stent and/or spread the crimping force more uniformly over the stent. Each crimping member has at least one member.

The invention also relates to methods of crimping a stent to a catheter using a loop based stent crimper. Generally, a stent disposed about a catheter is inserted into the one or more loops of the stent crimping device. The diameter of the loop is then reduced by pulling on one or more of the loop ends thereby crimping the stent to the catheter.

BRIEF DESCRIPTION OF THE SEVERAL VIEWS OF THE DRAWING(S)

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, the term stent refers to stents, stent-grafts, grafts and other endoluminal prostheses whether self-expanding, balloon expandable, self-expanding and balloon expandable, or otherwise expandable as are known in the art. Furthermore, where reference is made to crimping a stent, the invention specifically contemplates crimping stents, stent-grafts, grafts and other endoluminal prostheses.

Also, for the purposes of this disclosure, the term 'stent bearing region of a catheter' and similar terms refer to the portion of a catheter tube about which a stent is to be mounted or is mounted. In the case of balloon expandable stents, the terms refer to the portion of the catheter tube and balloon about which the stent is to be mounted or is mounted.

Finally, it is understood that the term 'crimping' and its cognates refer to a reduction in size or profile of a stent. When reference is made to crimping a stent to a catheter, a balloon may be situated between the stent and the catheter tube or the stent may be crimped to a region of a catheter tube directly. The stent may also be crimped, absent a catheter, within the context of this disclosure, by reducing it in size.

Figure 1:
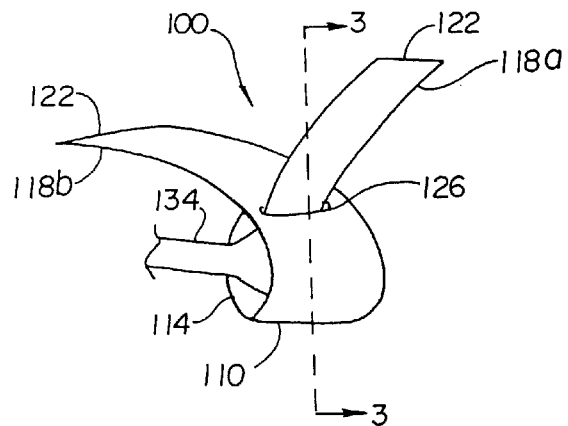
FIG. 1 is a fragmentary perspective detail view of an inventive stent crimper with a catheter disposed therein.

FIG. 1 shows an embodiment of a stent crimper, shown generally at 100, which comprises a crimping member 110 disposed in a loop 114. Two pulling members 118a, b extend from loop 114. Pulling members 118a, b terminate in pulling ends 122. Pulling members 118a, b are depicted as substantially rectangular members. Other shaped pulling members may also be employed in the practice of the invention including pulling members which taper inward, pulling members which taper outward and curved pulling members.

Figure 2:
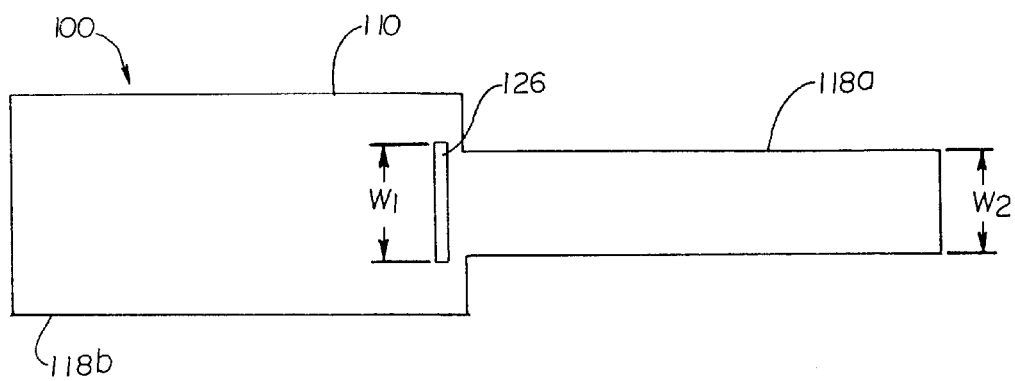
FIG. 2 is a top plan view showing die cut blank profile thereof.

A flat plan view of the stent crimper is shown in FIG. 2. Crimping member 110 has an opening 126 therethrough sized to accommodate pulling member 118a. Although opening 126 is depicted as a slot, other shaped openings may be used. Desirably, the shape of the opening will be chosen to accommodate the specific shape of pulling member 118a. More specifically, the width $W_1$ of opening is desirably sized slightly larger than the width $W_2$ of pulling member 118a.

Figure 3:
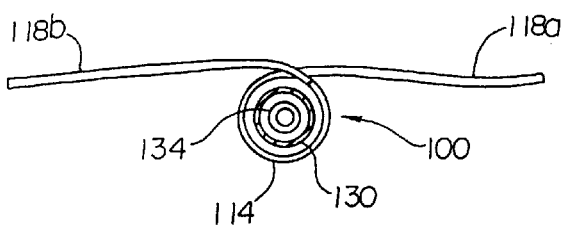
FIG. 3 is a side elevational view thereof shown in assembly.
Figure 4:
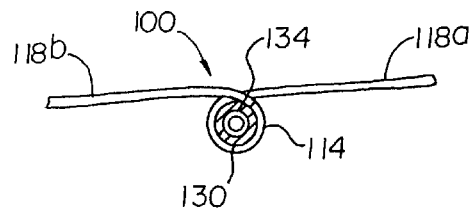
FIG. 4 is a view of the crimper of FIG. 3 after a crimping force has been applied to the stent.

In use, as depicted in FIGS. 1, 3 and 4, a stent 130 disposed about a desired portion of a stent delivery catheter 134 is inserted into loop 114. Pulling members 118a and 118b are moved in opposite directions relative to each other to reduce the diameter of loop 114. FIG. 3 depicts the stent and catheter loaded into stent crimper 100 prior to the application of a crimping force. FIG. 4 depicts the same stent and catheter after a crimping force has been applied thereto by moving pulling member 118a and 118b in opposite directions relative to one another. Loop 114 is seen to have a reduced diameter as compared with its diameter immediately preceding the crimping. Loop 114 is in crimping contact with stent 130 which, in turn, is in crimping contact with catheter 134.

The crimping action may result from moving both pulling members in opposite directions or moving a single pulling member while fixing the second pulling member in place to effect a relative movement between the two pulling members resulting in a shrinking of the loop.

Following crimping of the stent, the stent and catheter may be released by moving pulling members 118a and 118b toward one another to increase the diameter of loop 114.

Suitable materials for the stent crimper include rollable materials. One material which is particularly well suited for use in the present invention is paper which has been stiffened but which, nevertheless, is rollable. Suitable papers include card stock. Desirably, the paper will be from about 40 lb. card stock to about 90 lb. card stock. Coated papers may also be used. A permanent curl may be pressed into the paper by inserting a mandrel in the loop and reducing the loop diameter by pulling the pulling members apart. Other high strength papers may be used as well. More generally, other suitable materials may be used as well as long as they are rollable, yet sufficiently rigid not to deform upon application of the crimping force to the stent. Suitable materials include polymeric materials including polyesters, polyamides and polyethylenes. Other suitable materials include metals such as clock spring.

Pulling members 118a, b may also be provided with a gripping means at pulling ends 122. The gripping means may be ergonomically contoured to facilitate hand gripping and pulling of the pulling members.

Figure 5:
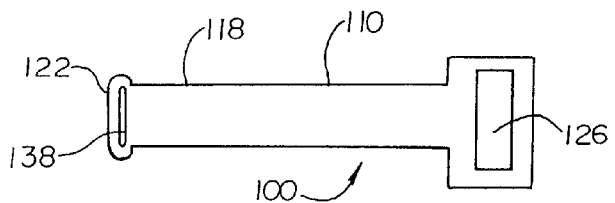
FIG. 5 is a view similar to that of FIG. 2 showing an alternate die cut profile thereof.
Figure 6:
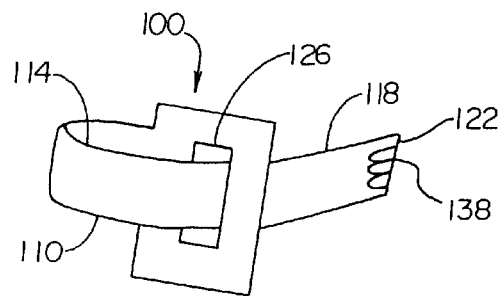
FIG. 6 is a view perspective detail view thereof erected.

Another embodiment of the invention is shown in the flat in FIG. 5 and a related embodiment shown in crimping configuration in FIG. 6. The embodiment of FIGS. 5 and 6 differs from that of FIGS. 1–4 in that opening 126 is disposed substantially at one end of crimping member 110.

FIGS. 5 and 6 also show two possible gripping means 138. The gripping means of FIG. 5 is a handle with an opening therein for fingers and the gripping means of FIG. 6 is a surface with indentations thereon designed to accommodate fingers. The gripping means may be smooth or suitably textured to facilitate gripping.

Figure 7:
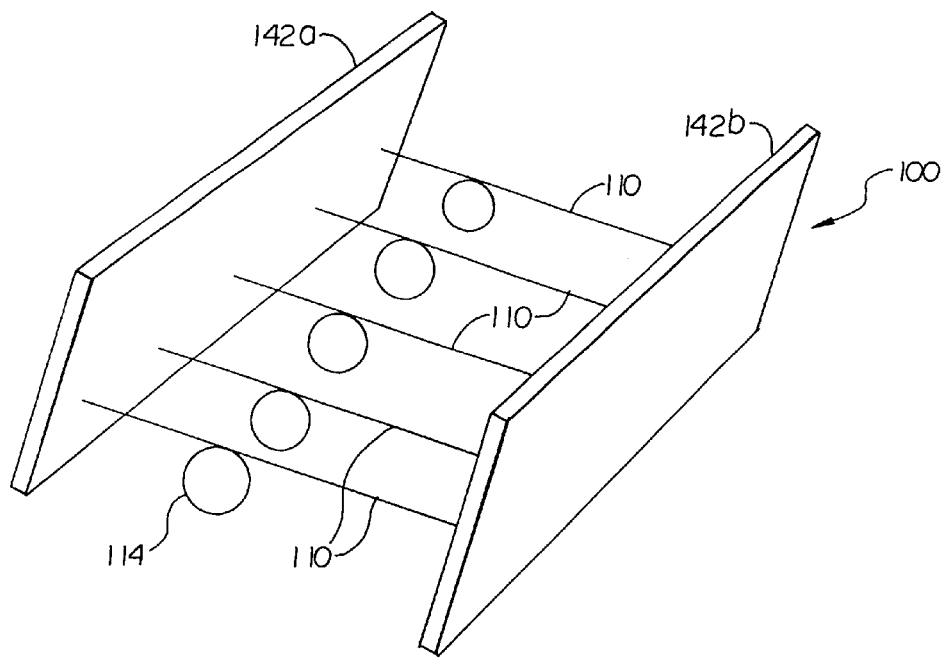
FIG. 7 is a simplified perspective view of another inventive stent crimper.

Another embodiment of the invention is shown generally at 100 in FIG. 7. A plurality of crimping members 110 extend from a first holder 142a to a second holder 142b. Each crimping member 110 is disposed in a loop 114. The embodiment of FIG. 7 employs five crimping members.

Figure 8:
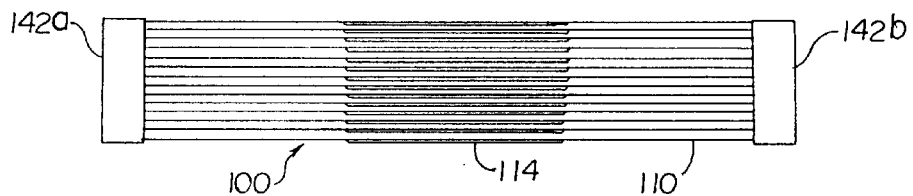
FIG. 8 is a simplified top plan view of a stent crimper similar to that of FIG. 7.

Additional or few crimping members may also be used. A top view of a crimper similar to that shown in FIG. 7 is depicted in FIG. 8. The crimper of FIG. 8 is constructed of more crimping members than the crimper of FIG. 7. The number of crimping members chosen will depend on the width of the crimping member relative to the length of the stent and the degree of uniformity desired in the crimp. In order to assure a uniform crimp, it is generally desirable to have more crimping members. If wider crimping members are used, however, fewer members may be necessary to achieve a uniform crimp.

In the spirit of the invention, a crimping device using only single crimping member may be constructed using the crimping member of FIGS. 1–4 mounted in the holders of FIG. 7. In such an embodiment, the presence of opening 126 in the crimping member is optional.

The invention also contemplates spacing the crimping members to result in a non-uniform crimp. This is particularly desirable where certain parts of the stent are to be crimped to a greater extent than other parts. One such application is the additional crimping of a stent at the end portions of the stent to minimize flaring of the stent ends as discussed below. Another such application is crimping in the presence of stent retention devices such as mounting rings as discussed below.

Desirably, the crimping member in the embodiments of FIGS. 7 and 8 will be a wire. The wire may be coated to avoid marring of the stent. Other suitable materials include fibers and cords. The invention further contemplates the use of other materials such as windable or rollable strips, ribbons or sheets of material, whether made of metal, plastic (polymeric) or other materials.

Figure 9:
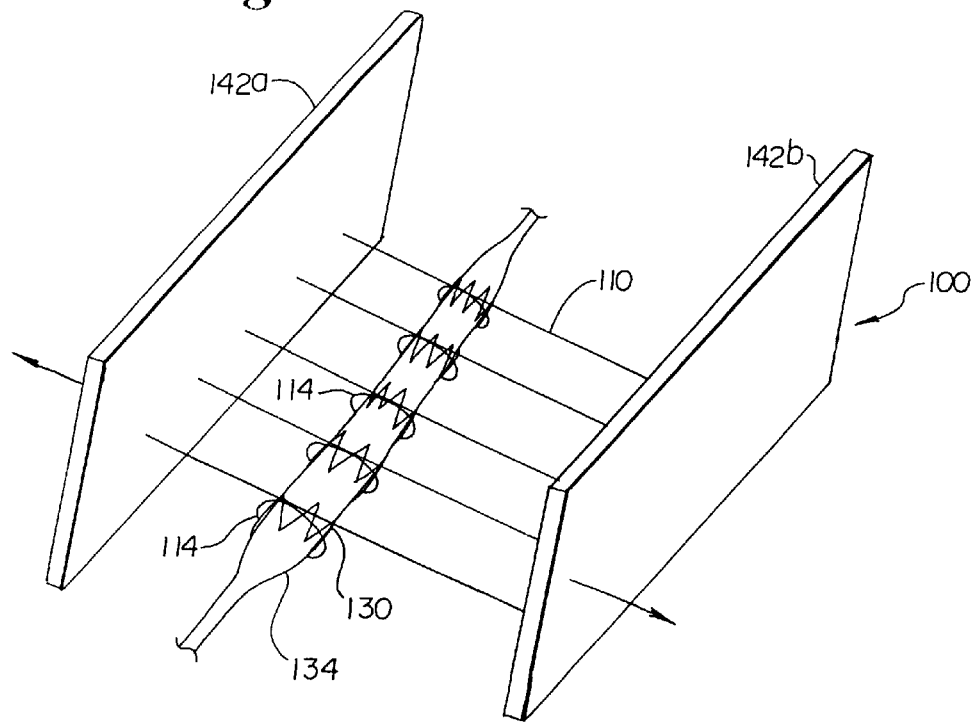
FIG. 9 is a perspective view of the subject of FIGS. 7 and 8 in assembly with fragmentary associated parts.

In use, as shown in FIG. 9, a stent 130, disposed about a desired portion of a stent delivery catheter 134, is inserted through loops 114. As first and second holders 142a, b are moved relative to each other in opposite directions, the loop diameters are decreased thereby crimping the stent to the catheter.

The invention also contemplates the use of an optional sleeve to protect the stent and to facilitate the spreading of the crimping force thereby increasing the uniformity of the crimp. An embodiment with such a sleeve is shown generally at 100 in FIG. 10. Crimping member 110 is disposed in a loop 114 about sleeve 146. Two pulling members 118a, b extend from loop 114. Pulling members 118a, b terminate in pulling ends 122.

Figure 10:
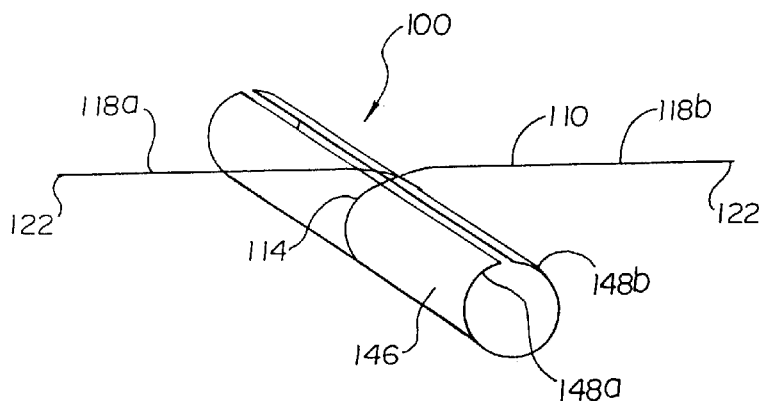
FIG. 10 is a simplified perspective view of another inventive stent crimper.

Sleeve 146 may be made of a variety of rollable or flexible materials. In a desired embodiment, sleeve 146 is made of springsteel or clock spring. Elastically deformable materials including other metals and polymeric materials such as polyester, polyamide, polyethylene and card stock may be used as well. As shown in FIG. 10, sleeve 146 is formed of a rolled sheet of material. Although the sheet is rolled into a tube, edges 148a, b are not joined together. As the diameter of the sleeve is reduced, one of edges 148a, b will ride up on the other. Desirably, the innermost of edges 148a, b will have a full chamfer so that the edge will slide smoothly over the stent. It is desirable that the entirety of the stent be in contact with the sleeve. More desirably, the sleeve will be wrapped around with one and a half turns so that for half of the circumference of the sleeve, the sleeve forms a double layer.

The sleeve shown in FIG. 10 may also be used in other embodiments of the invention disclosed herein.

The crimping device of FIG. 10 may also employ a plurality of pulling members. Where are a plurality of pulling members are employed, it is desirable that adjacent pulling members be interconnected, as shown in the embodiment of FIG. 11, to allow for a substantially uniform pulling force along the length of the sleeve.

Figure 11:
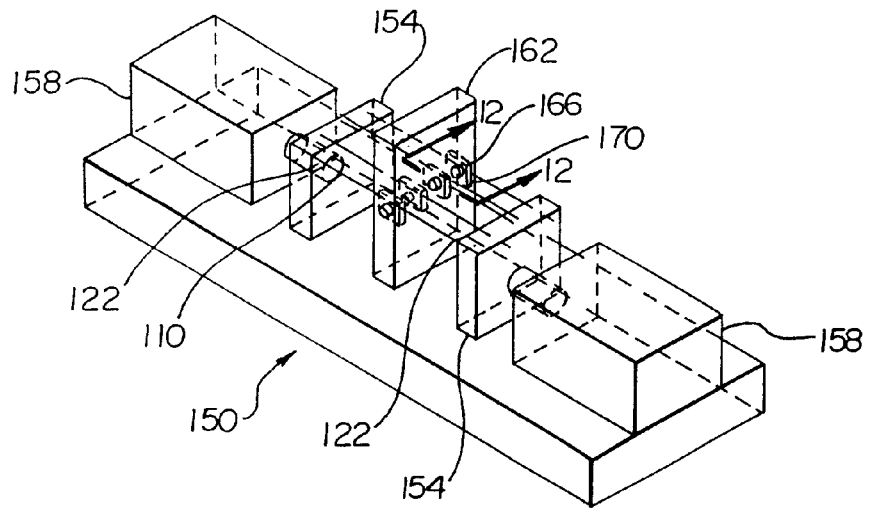
FIG. 11 is a perspective view of an inventive stent crimper.

The stent crimper of FIG. 11 comprises a support member 150 for supporting a sleeve and facilitating pulling. Support member 150 comprises a base with two pulling blocks 154 slidingly mounted thereon. Other more ergonomic designs may be substituted for the pulling blocks shown. Pulling blocks 154 are in communication with pulling member support blocks 158. Each end 122 of each pulling member 110 is mounted in a pulling member support block 158. A sleeve support block 162 is disposed between pulling member support blocks 158. Sleeve support block 162 has a bore 166 therethrough for supporting a sleeve similar to that shown at 146 in FIG. 10. The presence of the sleeve is desirable although not necessary. Sleeve support block 162 is also provided with openings 170 therethrough in a direction substantially perpendicular to bore 166. Each pulling member 110 extends through an opening 170.

Figure 12:
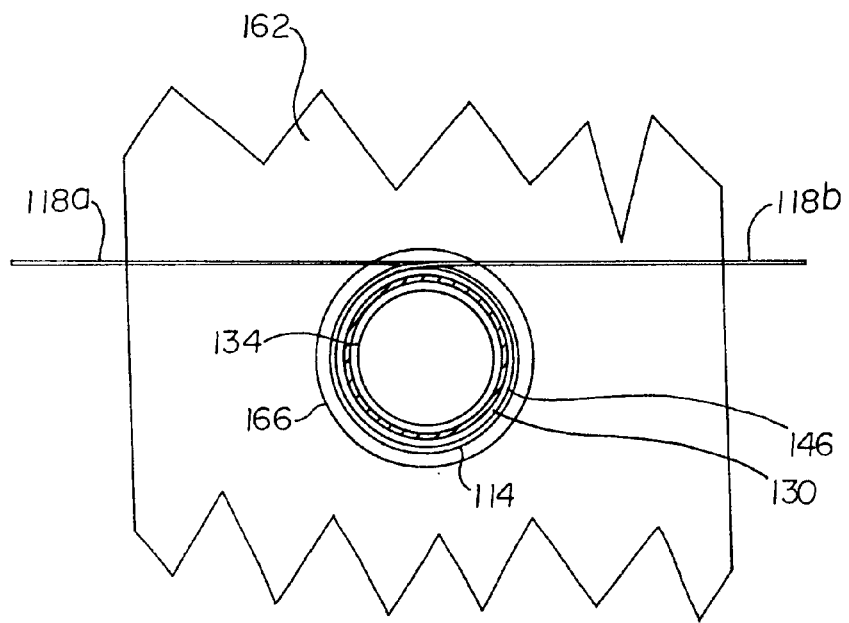
FIG. 12 is a cross-sectional view of FIG. 11 through line 12—12.

In use, a stent disposed about a desired portion of a stent delivery catheter (not shown) is inserted into bore 166 and desirably into a sleeve such as that shown in FIG. 10. Pulling blocks 154 are then moved in opposing directions thereby reducing the diameters of loops 114 which in turn reduces the diameter of sleeve 146 and imparts a crimping force to the stent. FIG. 12 shows a cross-sectional view of the crimper along line 12—12 with stent 130 and catheter 134 loaded in sleeve 146.

Figure 13:
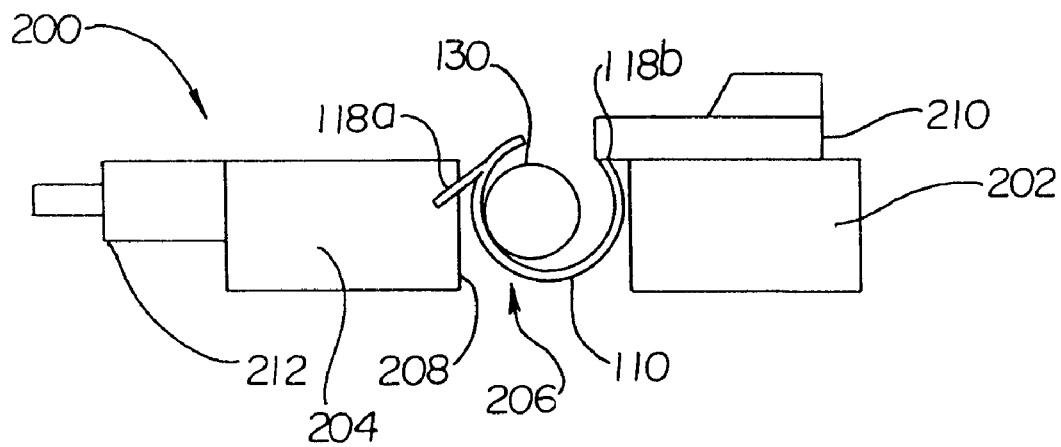
FIG. 13 is a side view of an inventive stent crimper apparatus prior to stent crimping.

In another embodiment of the invention, as shown in FIG. 13, the stent crimping apparatus shown generally at 200 includes a support frame having a first section 202 and a second section 204 separated by a groove 206. A stent crimping member 110 extends between first section 202 and second section 204. Stent crimping member 110 is formed of a rollable material which is capable of applying an inward force to a stent, desirably without significant deformation to the material. One end 118a of stent crimping member 110 is attached to an inside wall 208 of section 204 of the support frame. The other end 118b of stent crimping member 110 is attached to a movable carriage 210 extending from first section 202. Movable carriage 210 may be slid over groove 206 such that end member 118b passes over first member 118a. Desirably, movable carriage 210 will be slidably mounted to first section 202.

In use, a stent 130 is placed on crimping member 110. Movable carriage 210 is slid toward second section 204 of the support frame causing crimping member 110 to partially loop around stent 130. As crimp movable carriage 210 continues to move, an inward force is exerted on stent 130 reducing the stent in size.

Figure 14:
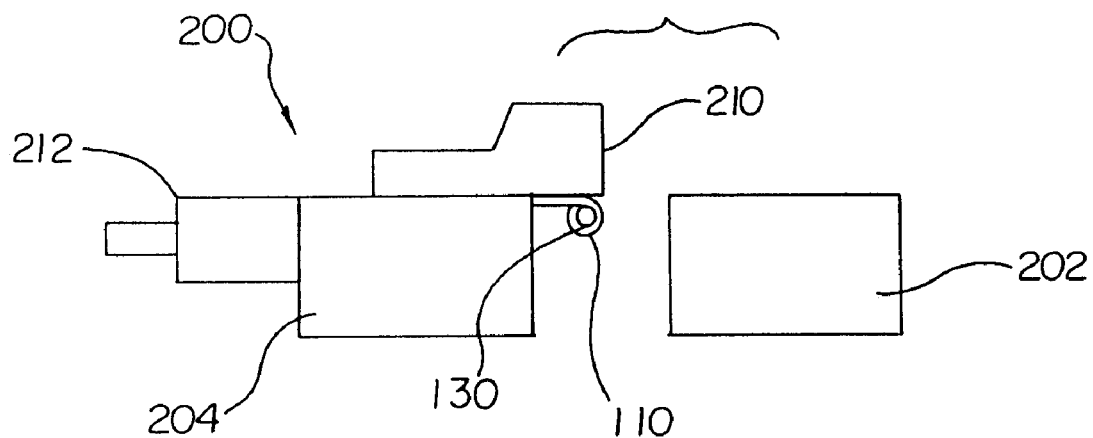
FIG. 14 is a view of the stent crimper shown in FIG. 14 after the stent has been crimped.

In a preferred embodiment the stent crimping apparatus shown in FIGS. 13 and 14 includes a chilled air supply 212 which is particularly desirable for use with shape memory stents. Nitinol stents, for example, may be chilled to the martensitic state prior to or during crimping.

After the stent is reduced in size in the manner shown in FIGS. 13–14 it may be desirable to compress the stent further. To that end, the stent compressing apparatus shown generally at 218, in FIGS. 15–16 utilizes an opposable pair of contoured or C-shaped jaws 220, 222. Jaw 220 is fixed and holds stent 130 in position. Jaw 222 is moveable relative to jaw 220 and is pushed toward jaw 220 when lever 224 is pulled upward as shown in FIG. 16. When jaws 220, 222 are brought together, the contoured surfaces of the jaws provide a uniform and even compression force over the entire circumference of the stent. The apparatus employs a plurality of biasing members 225, 226 and 228 to provide precise control and compressive strength to moveable jaw 222, thereby ensuring that the stent is compressed to the extent desired while ensuring that the stent is not subject to excessive force which could damage the stent.

Figure 15:
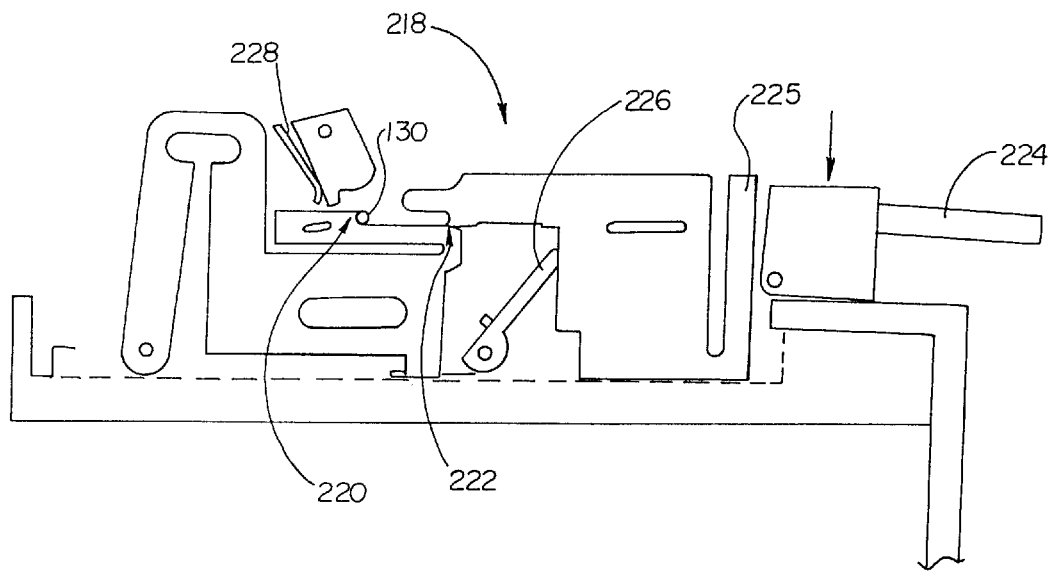
FIG. 15 is a side view of a mechanism to compress a stent.
Figure 16:
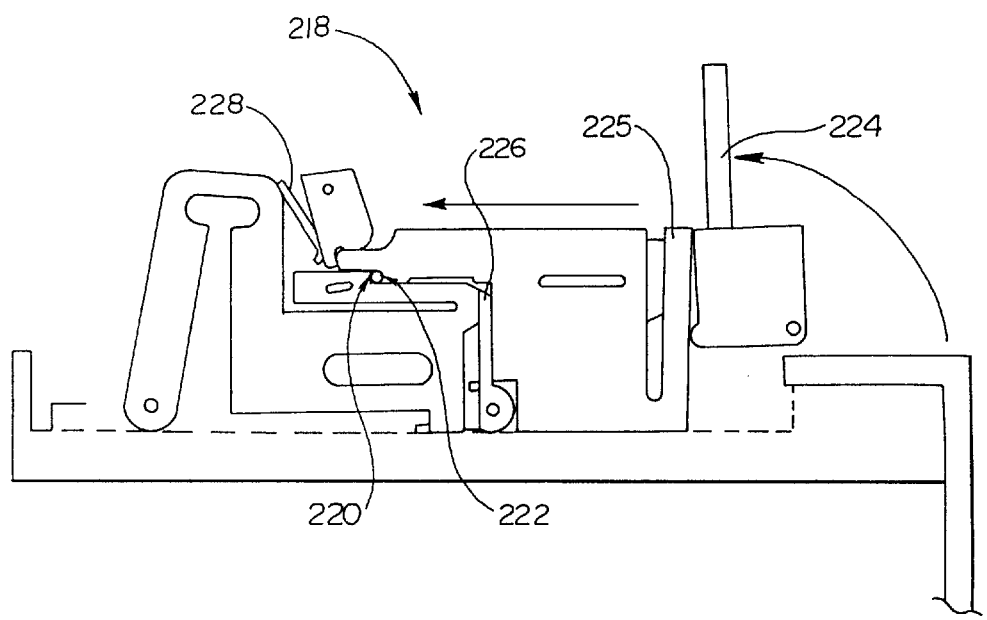
FIG. 16 shows the mechanism shown in FIG. 15 after compression of the stent.

The apparatus of FIGS. 15 and 16 may also be used to pre-crimp a stent prior to crimping with any of the other inventive crimpers disclosed herein.

In another embodiment, the invention is directed to a method of crimping a stent to a catheter. In the practice of the method, a stent disposed about a catheter is provided. At least one pulling member of reducible diameter is disposed about the periphery of the stent to form a loop about the stent. The pulling member has at least one pulling end. The diameter of the loop is then reduced by pulling on one or both ends of the pulling members thereby crimping the stent. This may be accomplished by fixing one pulling end in place and moving the other pulling end or by moving both pulling ends in opposing directions.

The invention also contemplates the use of an additional protective sleeve to prevent direct contact between the stent and the crimping device. This may minimize or eliminate any marring or nicking of the stent by the crimping member. A suitable sleeve comprised of polymeric tubing is described in copending, commonly assigned U.S. application Ser. No. 08/951,550. In addition to the materials discosed therein for the sleeve, the sleeve may be formed of polyester, polyamide, nitinol, kevlar, polypropylene or polyurethane. Desirably, the sleeve will be in braid form, with a pick count of between about 20 and 90 picks/inch and preferably about 55 picks/inch, to prevent direct contact between the stent and the crimping device. In addition to protecting the stent, the protective sleeve may also be used to reduce the stent in size prior to the stent being crimped as described in U.S. application Ser. No. 08/951,550.

Where the stent is crimped to an inflatable balloon disposed about a catheter, the crimping process may be supplemented by the additional steps of at least partially inflating the balloon so that at least a portion of the balloon engages the stent prior to or while applying an inward force to the stent and optionally deflating the balloon in tandem with the application of an inward force to the stent. These additional steps may result in superior engagemet of the balloon and stent.

The inventive devices may also be used to pre-crimp a stent in the absence of a catheter. The pre-crimped stent may then be crimped onto a catheter.

In addition to being directed to the specific combinations of features claimed below, the invention is also directed to embodiments having other combinations of the features described above and claimed below. The invention is further directed to methods of crimping in which any of the individual crimping modalities disclosed herein is combined in sequence with any other crimping modality disclosed herein and/or with any of the crimping modalities described in the commonly assigned, copending U.S. application Ser. No. 08/951,550 all of which are directed to stent crimpers and all of which are incorporated herein in their entirety by reference. Thus, a stent may be pre-crimped using one crimping technique and further crimped using another crimping technique.

The above disclosure is intended to be illustrative and not exhaustive. This description will suggest many variations and alternatives to one of ordinary skill in this art. All these alternatives and variations are intended to be included within the scope of the attached claims.

In addition to being directed to the specific combinations of features claimed below, all possible alternative dependent combinations of the features recited above or in the dependent claims, whether written in multiple dependent form or not, should be considered to be within the scope of the invention. Those familiar with the art may recognize other equivalents to the specific embodiments described herein which equivalents are also intended to be encompassed by the claims attached hereto.

We claim:

1. A stent crimper comprising:
   a support frame, the support frame having a first section and a second section, and a gap extending therebetween;
   a movable carriage movably mounted on the first section of the support frame, the movable carriage capable of moving back and forth from the first section to the second section and
   a crimping member for receiving a stent thereon, the crimping member disposed in the gap, a first end of the crimping member extending from the movable carriage, a second end of the crimping member extending from the second section, the crimping member forming a loop when the movable carriage is moved toward the second end of the crimping member.

2. The stent crimping apparatus of claim 1 further including a cooling means for cooling a stent to a predetermined temperature.

3. The stent crimping apparatus of claim 2 wherein the cooling means comprises a reservoir and applicator of chilled air.

4. method of crimping a stent comprising the following steps:
   providing a crimping apparatus as in claim 1;
   placing a stent on the crimping member;
   sliding the carriage from the first section to the second section so as to form a reducible diameter loop which imparts an inward force to the stent.

5. The method of claim 4 further comprising the steps of placing the stent into a stent compressing apparatus having an opposable pair of jaws, the jaws having contoured surfaces constructed and arranged to receive and uniformly compress the stent when the stent is placed within the jaws and the jaws are brought together; and
   bringing the opposable jaws together with a predetermined force to reduce the size of the stent.

* * * * *